(12) United States Patent
Vandaele

(10) Patent No.: US 8,192,689 B2
(45) Date of Patent: Jun. 5, 2012

(54) METHOD FOR IMPROVING A POLYMERIZATION REACTION BY TAKING OUT AND ANALYSING A SAMPLE

(75) Inventor: Hugo Vandaele, Sint-Andríes (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

(21) Appl. No.: 13/022,012

(22) Filed: Feb. 7, 2011

(65) Prior Publication Data

US 2011/0142720 A1 Jun. 16, 2011

Related U.S. Application Data

(60) Continuation of application No. 12/391,052, filed on Feb. 23, 2009, now abandoned, which is a continuation of application No. 11/502,005, filed on Aug. 9, 2006, now abandoned, and a division of application No. 12/862,655, filed on Aug. 24, 2010, which is a division of application No. 12/243,346, filed on Oct. 1, 2008, now abandoned, which is a division of application No. 11/057,715, filed on Feb. 14, 2005, now abandoned.

(60) Provisional application No. 60/544,846, filed on Feb. 13, 2004.

(30) Foreign Application Priority Data

Feb. 13, 2004 (EP) .................................. 04100599

(51) Int. Cl.
*B01J 19/00* (2006.01)
*G01N 1/00* (2006.01)

(52) U.S. Cl. ........... 422/131; 422/62; 422/68.1; 422/83; 422/119; 73/863.84; 73/863.86; 73/863.71; 526/59

(58) Field of Classification Search .................. 422/131, 422/62, 68.1, 83, 119; 73/863.84, 863.86, 73/863.71; 526/59
See application file for complete search history.

(56) References Cited

U.S. PATENT DOCUMENTS

| | | | | |
|---|---|---|---|---|
| 3,324,093 | A * | 6/1967 | Alleman | 526/64 |
| 3,556,730 | A * | 1/1971 | Mitacek | 436/85 |
| 6,566,460 | B1 * | 5/2003 | Salmon | 526/64 |
| 2003/0161765 | A1 * | 8/2003 | Kendrick et al. | 422/132 |

* cited by examiner

*Primary Examiner* — Walter D Griffin
*Assistant Examiner* — Lessanework Seifu

(57) ABSTRACT

The invention relates to a device for taking out and analyzing a sample from a polymerization reactor comprising one or more sample conduits (2), for taking a sample out of said reactor and for conducting said sample to one or more sample flash tanks (3), whereby said conduits each are in communication with said reactor (19) and each are provided with at least two sampling valves (4, 5); comprising one or more sample flash tanks (3), for separating said solid particles and evaporated gas, whereby said sample flash tanks are connected to said conduits (2) and provided with means for analyzing said evaporated gas (7), and comprising one or more sample receivers (6), for purifying said solid particles, whereby said receivers are connected to said sample flash tanks (3) and provided with means (8) for analyzing said solid particles. The invention further relates to a method for improving a polymerization reaction in a polymerization reactor.

15 Claims, 3 Drawing Sheets

METHOD FOR IMPROVING A POLYMERIZATION REACTION BY TAKING OUT AND ANALYSING A SAMPLE

CROSS-REFERENCE TO RELATED APPLICATIONS

This application is division of U.S. patent application Ser. No. 12/862,655, filed Aug. 24, 201, a continuation of U.S. patent application Ser. No. 12/391,052, filed Feb. 23, 2009, a division U.S. patent application Ser. No. 12/243,346, filed Oct. 1, 2008, a continuation of U.S. patent application Ser. No. 11/502,005, filed Aug. 9, 2006, a continuation of U.S. patent application Ser. No. 11/057,715, filed Feb. 14, 2005, and claims priority from U.S. Provisional Pat. Appl. Ser. No. 60/544,846, filed Feb. 13, 2004.

FIELD OF THE INVENTION

This invention relates to process control. In a first aspect, the invention relates to a device for taking out and analysing a sample from a polymerisation reactor, in particular a polymerisation reactor suitable for polymerising ethylene. In another aspect the invention relates to a method for improving a polymerisation reaction in a polymerisation reactor during a process for preparing bimodal polyethylene.

BACKGROUND OF THE INVENTION

In a typical polymerisation reaction, monomer, diluent, catalyst, co-catalyst and optionally co-monomer and hydrogen are fed to a reactor where the monomer is polymerised. The diluent does not react but is typically utilised to control solids concentration and also to provide a convenient mechanism for introducing the catalyst into the reactor. The reactor effluent, a mixture of polymer, diluent, unreacted (co-)monomer and hydrogen, is removed from the reactor and fed to a flash tank where the polymer is separated from the diluent and unreacted (co-)monomer and hydrogen. Typically, catalyst will be contained in the polymer.

Polymerisation processes of ethylene may be carried out in loop reactors. In the polymerisation reaction of ethylene, different reactants including the monomer ethylene, a light hydrocarbon diluent such as isobutane, a catalyst and optionally, a co-monomer such as hexene-1 and hydrogen are fed to a reactor. When polymerising ethylene, in the presence of a suspension of catalyst in diluent, said diluent having low solubility for the polymer, the polymer is produced in the form of solid particles, insoluble in the diluent. The contents of the reactor are circulated continuously with a pump to avoid deposition of polymer on the walls of the reactor. Slurry, consisting of the reactants and polyethylene powder, is typically collected in one or more settlings legs of the polymerisation reactor and discharged continuously to a flash tank, through flash lines, where most of the light hydrocarbon diluent and unreacted ethylene evaporates, yielding a dry bed of polyethylene in powder form. The powder is discharged to a purge drier in which the remaining light hydrocarbon and co-monomer are removed. Then the powder of polyethylene is transported to a finishing area where various stabilisers and additives are incorporated. Finally it is extruded into pellets.

For obtaining polymer having suitable properties, it is essential in a polymerisation reaction to control the reaction conditions and input component quantities in the reactor. For doing so, it is conventional to sample the reactor contents and control several of the variables of the process in response with the analysis of the sample.

Several methods have been described to take samples from the reactor contents. Generally the reactants in loop-type reactors are propelled at relatively high velocities in order to maintain the catalyst and particulate polymer produced in a suspended state and to prevent deposition or growing of polymer on the reactor walls. It is therefore necessary that no vapor phase is present in the reactor where polymer might grow. In order to take a sample from such reactors, generally a standpipe is placed in the uppermost portion of the reactor to collect slurry. However, the slurry in said standpipe is generally not in equilibrium with the reactants, and hence it is almost entirely impossible to obtain a representative sample.

A vapor sample may be taken from the flash tank. However, sampling of gases from flash tanks has several disadvantages. In polymerisation plants using flash tanks which are connected to a reactor by means of flash lines and settling legs, the settling legs themselves can present problems. Conventional settling legs have sections in which polymer can collect while waiting for next dump cycle for transferring the slurry to a flash tank. The collected polymer can melt over time and deposit on the inside walls of the settling leg. In addition, during collection of the slurry in the settling legs and before dumping it to the flash tank, the polymerisation reaction still continues. Also, there is a lag in time between recovery of slurry in the settling legs and further processing of the slurry to the flash tank. As a consequence thereof, reaction conditions, which are monitored after transfer of the slurry in the flash tank, are different from the reaction conditions in the reactor. Analysis of a gas sample taken from the flash tank does not provide updated information on the reaction conditions in the polymerisation reactor and will result in an inaccurate analysis of the gas composition in the polymerisation reactor.

U.S. Pat. No. 3,556,730 refers to a sampling apparatus for taking a sample comprising liquid, dissolved gas and suspended particulate solids from a reactor into a fixed volume chamber. The reaction fluid in the chamber is then rendered non-reactive by immediately adding a predetermined volume of reaction termination fluid. The non-reactive sample is automatically discharged into a separation chamber from which part of the dissolved gas and liquid is continuously analysed.

U.S. Pat. No. 6,042,790 describes an apparatus and method for maintaining unreacted monomer concentration in a polymerisation reactor. In a polymerisation process utilising a high pressure flash to separate polymer from unreacted monomer contained in the effluent stream from the reactor, the concentration of unreacted monomer in the reaction effluent is determined by withdrawing from the reactor an effective analysing amount of effluent, exposing the amount to a low pressure flash and analysing the vaporised portion to determine the concentration of monomer. However, the described apparatus and method do not allow to take solid particles out of the reactor and to analyse these.

U.S. Pat. No. 4,469,853 provides a method for preparing polyolefins. A step in this method consists of detecting the concentrations of olefin and hydrogen in the gas phase within the reactor by gas chromatography. However, the described apparatus and method do not allow to take solid particles out of the reactor and to analyse these.

U.S. Pat. No. 6,037,184 discloses a method and apparatus for taking a sample out of a flowing suspension formed by polymer particles and hydrocarbon diluent in a olefin polymerization process. The apparatus relies on the use of a filter which is placed either straight to the wall of the loop reactor, whereby a sample is taken straight from the loop reactor, or in a transfer pipe which connects two loop reactors. A sample is taken out of the reactor and transferred to a vaporizing pressure reducer. The vaporized sample is then introduced in a wax separation vessel and further in a wax removal vessel. However, the sample taken out of the loop reactor does not contain solid particles. Analysis of said sample is therefore not fully representative for the reaction conditions in the loop reactor. In addition, in embodiments wherein a sampling apparatus is provided in a transfer pipe which connects two loop reactors, reaction conditions, which are monitored after transfer of the slurry in the transfer pipe, are different from the reaction conditions in the loop reactor. Thus, analysis of a sample taken from such transfer pipe does not provide fully updated information on the reaction conditions in the polymerisation reactor.

A drawback in the above-described devices and methods is that they do not allow the control of several different variables of the polymerisation process, such as e.g. monomer, co-monomer and hydrogen in the gas phase and properties of the polymerisation product such as the melt flow index and density, in response with the analysis of the sample.

In addition, the above-described methods and devices are not suitable for controlling the polymerisation reaction in system wherein bimodal polyethylene is prepared, i.e. in system comprising two interconnected polymerization reactors. In particular, the above-described methods and devices do not provide for a representative sampling of a first polymerisation reactor in such bimodal system.

In view hereof, it is clear that there remains a need in the art for providing a more accurate sampling system for taking and analysing a sample from a polymerisation reactor. It is therefore an object of the present invention to provide a device capable of taking out a sample from a polymerisation reactor and accurately analysing said sample. It is further an object of the invention to provide a device capable of taking out a sample from a polymerisation reactor, which consists of two reactors being connected in series. Another object of the invention is to provide a sampling system for taking and analysing a sample from a polymerisation reactor wherein the solid as well as the gaseous phase of said sample are analysed.

It is another object of the present invention to provide a method for improving a polymerisation reaction in a polymerisation reactor. In particular, the invention aims to provide a method for improving a polymerisation reaction for preparing bimodal polyethylene in a polymerisation reactor, which consists of two reactors being connected in series.

SUMMARY

In accordance with the present invention a sampling device is provided for taking out and analysing a sample from a polymerisation reactor containing reactive fluid, said sample comprising solid particles suspended in said reactive fluid. The device according to the invention comprises:
  one or more sample conduits, for taking a sample out of said reactor and for conducting said sample to one or more sample flash tanks, whereby said conduits each are in communication with said reactor and each are provided with at least two sampling valves,
  one or more sample flash tanks for separating said solid particles and evaporated gas, whereby said sample flash tanks are connected to said conduits and provided with means for analysing said evaporated gas, and
  one or more sample receivers for purifying said solid particles, whereby said receivers are connected with said sample flash tanks and provided with means for analysing said solid particles.

In another aspect the invention relates to the use of a sampling device according to the invention for taking a sample out of a polymerisation reactor and for analysing said sample. Chemical and physical analysis of samples obtained from the reactor by use of a sampling device according to the present invention provide accurate and representative information of the reaction conditions inside the reactor as well as the properties of the composition of the gas phase and the solid particles in the reactor. Because of the negligible residence time in the sampling device, samples taken by means of the present sampling device give an accurate and representative picture of the conditions inside the reactor at sampling time.

In addition, the invention further relates to the use of the present sampling device for improving a polymerisation reaction in a polymerisation reactor. The sampling device according to the present invention is usable for taking a sample from an individual reactor and determining the reaction conditions in said reactor. Preferably, samples are analysed frequently, in order to accurately follow up the polymerisation reaction in the reactor. Based on the analyses results obtained, one can adapt operational reaction parameters in the reactor in order to optimise the polymerisation reaction and to obtain a polymer having suitable properties and a desired product quality.

In addition, the sampling device according to the invention can also be used for improving a polymerisation reaction in a polymerisation reactor that consists of two reactors that are connected to each other, preferably in series. Such reactor configuration advantageously allows applying different operational conditions in the different reactors, which allows playing on the properties of the final product. The problem in such reactor configuration however, consists of correctly determining the suitable moment on which a reaction product has certain desired properties and is suitable for being transferred from a first to a second reactor and from the second reactor to means for further processing. Transfer of a reaction product having sub-optimal properties from such second reactor to further processing means considerably reduces product quality. Using the sampling device according to the present invention in such configuration allows frequent analysis and follow-up of the operational reaction conditions in both reactors. Thus, by frequently taking and analysing samples from a first and a second reactor the present invention allows to adapt the reaction conditions in the first as well as in the second polymerization reactor. Moreover, the sampling device according to the invention can also be used for improving the polymerisation reaction conditions in a second slurry loop polymerisation reactor, by taking a sample out of a first slurry loop polymerisation reactor which is connected thereto, and by analysing said sample. The suitable moment for transferring the reaction product from the second reactor to further processing can be correctly determined, and a final reaction product having optimal properties is supplied from the second reactor to further processing.

In another aspect, the present invention relates to methods for improving a polymerisation reaction in a polymerisation reactor. The term "improving a polymerisation reaction in a polymerisation reactor" as used herein relates to the following up of a polymerisation reaction and the fine-tuning—if required—of operational reaction conditions thereof in an individual reactor, in order to improve the efficiency of the polymerisation reaction and/or the product quality in this individual polymerisation reactor. This term also refers to the following up of a polymerisation reaction and the fine-tuning—if required—of operational reaction conditions thereof in two or more reactors which are connected to each other, preferably in series, such that the efficiency of the polymerisation reaction is ensured and that a final reaction product resulting from the polymerisation reaction in said reactors is fed at a suitable time and having optimal product quality to further processing means.

In an embodiment the present invention relates to a method for improving a polymerisation reaction for preparing polyethylene in a slurry loop polymerisation reactor, said method comprising the steps of
- a) taking a sample out of said reactor,
- b) analysing said sample to determine said reaction conditions in said reactor, and
- c) based on results obtained in step b), adapt reaction conditions in order to improve the polymerisation reaction in said reactor.

In another embodiment, the present invention relates to a method for improving a polymerisation reaction for preparing bimodal polyethylene in a first and in a second slurry loop polymerisation reactor which are connected to each other, said method comprising the steps of
- a) taking a sample out of said first reactor,
- b) analysing said sample to determine said reaction conditions in said first reactor, and
- c) based on results obtained in step b), adapt reaction conditions in said first reactor and in said second reactor in order to improve the polymerisation reaction in said first reactor and in said second reactor.

In another preferred embodiment, the invention relates to a method for preparing bimodal polyethylene in a first and in a second slurry loop polymerisation reactor, comprising the steps of:
- a) taking a sample out of said first reactor,
- b) analysing said sample to determine said reaction conditions in said first reactor,
- c) based on results obtained in step b), adapt reaction conditions in said first reactor in order to provide an optimised reaction product in said first reactor,
- d) transferring said reaction product from said first reactor to said second reactor,
- e) optionally, based on results obtained in step b), adapt reaction conditions in said second reactor in order to provide an optimised reaction product in said second reactor, and
- f) feeding at a suitable time said optimised reaction product from said second reactor to further processing means.

In another embodiment, the invention relates to a method for optimising the polymerisation reaction conditions for preparing bimodal polyethylene in a second slurry loop polymerisation reactor, connected to a first slurry loop polymerisation reactor, comprising:
- a) taking a sample out of said first slurry loop polymerisation reactor,
- b) analysing said sample, and
- c) based on results obtained in step b), adapt reaction conditions in said second reactor in order to provide an optimised reaction product in said first reactor.

In particular, in a preferred embodiment, the step a) in these methods of taking a sample comprises
providing a sample from said first reactor to a sample flash tank, by transferring said sample through a conduit connecting said first reactor to said sample flash tank,
separating in said sample flash tank solid particles from evaporated gas in said sample by controlling the pressure in said flash tank,
supplying said solid particles from said sample flash tank to one or more sample receivers, by transferring said solid particles through a conduit connecting said sample flash tank and said sample receivers, and
purifying said solid particles in said sample receivers, by degassing and drying.

Furthermore, in another preferred embodiment the analysis step b) in the present method comprises analysing evaporated gas obtained from said sample flash tanks with analysing means, and analysing solid particles obtained from said sample receivers with analysing means.

In another preferred embodiment of said method, said sample is taken out of a reactor part and analysed by means of a sampling device according to the present invention.

The sampling device and the method according to the invention are particularly useful in the polymerisation process of ethylene. Those skilled in the art will immediate recognise the many other effects and advantages of the present method and device from the detailed description and accompanying drawings provided below.

DETAILED DESCRIPTION OF THE FIGURES

DETAILED DESCRIPTION OF THE INVENTION

The invention is described in terms of the polymerisation of ethylene. Suitable "ethylene polymerisation" includes but is not limited to homo-polymerisation of ethylene, co-polymerisation of ethylene and a higher 1-olefin co-monomer such as butene, 1-pentene, 1-hexene, 1-octene or 1-decene. More in particular, the present invention is described in terms of the polymerisation of ethylene for manufacturing bimodal polyethylene (PE). "Bimodal PE" refers to PE that is manufactured using two reactors, which are connected to each other in series. However, the invention is applicable to any polymerisation reaction where it is desired to take and analyse a sample from a polymerisation reactor in an accurate way, or to improve the polymerisation reaction in the reactor.

In a preferred embodiment, ethylene polymerisation comprises feeding to a reactor the reactants including the monomer ethylene, a light hydrocarbon diluent, a catalyst and optionally a co-monomer and hydrogen. In an embodiment of the present invention, said co-monomer is hexene and said diluent is isobutane.

As used herein, the term "polymerisation slurry" or "polymer slurry" or "slurry" means substantially a two-phase composition including polymer solids and liquid. The solids include catalyst and a polymerised olefin, such as polyethylene. The liquids include an inert diluent, such as isobutane, with dissolved monomer such as ethylene, co-monomer, molecular weight control agents, such as hydrogen, antistatic agents, antifouling agents, scavengers, and other process additives.

Figure 1:
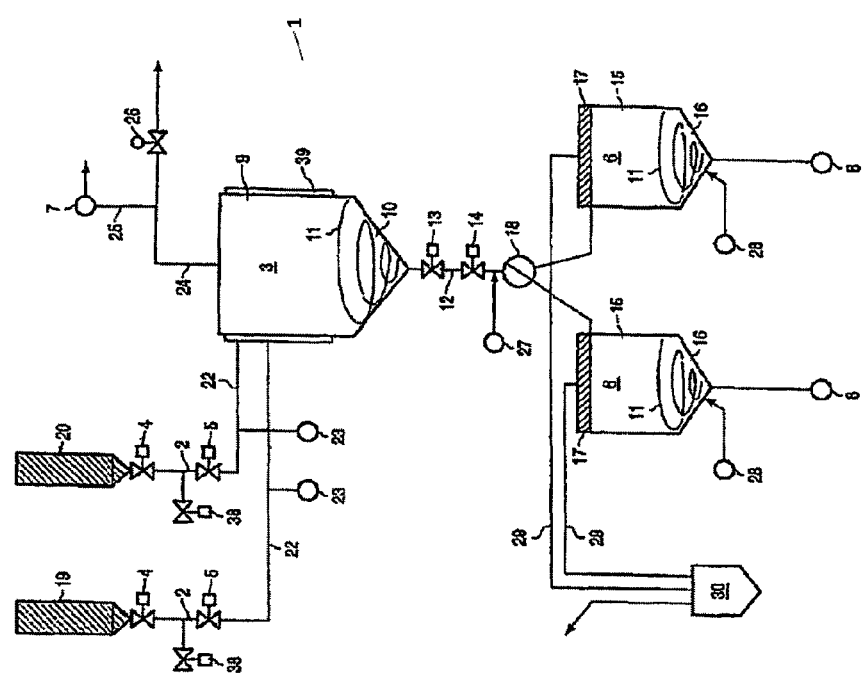
FIG. 1 represents a schematic view of an embodiment of a sampling device according to the present invention.

In a first aspect, the present invention relates to a sampling device for taking out and analysing a sample from a polymerisation reactor. Referring to FIG. 1, there is illustrated an embodiment of a sampling device 1 according to the invention. In a particularly preferred embodiment, the sampling device 1 according to the invention consists of two conduits 2, each connected to one sample flash tank 3, which is connected to two sample receivers 6, as illustrated on FIG. 1. However, it is clear that the present device may contemplate more conduits, sample flash tanks and/or sample receivers. It is clear from the present description that numbers of dimensions of the different parts of the sampling device can be related to the size of the polymerisation reactors and can be changed in function of the reaction sizes.

The term "sample" as used herein refers to a slurry sample that is taken out of the reactor. In the sample flash tank, most of the light hydrocarbon diluent, unreacted ethylene and co-monomer evaporates and is removed from the sample flash tank. A portion of the removed gas is taken for analysis. The solids. i.e. polyethylene in powder form, remaining in the sample flash tank are transferred to sample receivers in which remaining light hydrocarbon and co-monomer is removed and the resulting polyethylene powder is analysed. Thus, according to this invention, the sample is separated in a gas and a solid phase, which are both analysed.

Technically speaking, as used herein the terms "a reactor" or "a part of a reactor" are to be considered as equivalents. In view hereof, it shall be understood that embodiments of the present invention referring to a first and a second polymerisation reactor which are connected to each other, may also refer to embodiments referring to a first part and a second part (different from the first part) of a single polymerisation reactor. This means that embodiments of the invention referring to a first and a second polymerisation reactor which are connected to each other, and wherein a sample is taken out a first reactor and analysed in order to adapt the operational conditions of a second reactor, may also refer to embodiments wherein a sample is taken out of a first part of a single reactor and analysed in order to adapt the operational conditions in another part of said single reactor.

The device comprises one or more sample conduits 2, for taking a sample out of said reactor. An effective analysing amount of slurry is removed via two conduits 2 from a polymerisation reactor 19. In FIG. 1, it is illustrated that a sample is obtained from two separate reactors 19, 20, which are not interconnected. In a preferred embodiment said reactors consist of liquid full loop reactors. Loop reactors are known in the art and need not be described herein in detail. However, it should be understood that the present device can also be applied to take samples of reactors, in particular liquid full loop reactors, which are connected in series, as illustrated on FIG. 2. In a more preferred embodiment the device can be used on a polymerisation reactor comprising a first 19 and a second reactor 20 which are interconnected in series by one or more settling legs 21 of the first reactor 19 connected for discharge of slurry from the first reactor 19 to said second reactor 20, as illustrated on FIG. 2.

The sampling device according to the present invention may be placed at one of the elbows of the loop reactor or at other places. Preferably, the device 1 is positioned on an elbow of the reactor, but not in the proximity of the pump for continuously circulating the contents of the reactor through the reactor loops. For instance, on one of the elbows of such loop reactor 19, 20, one or more conduits 2 can be provided for removing a sample from the reactor and transferring such sample to a sample flash tanks 3. The conduits 2 each are in communication with said reactor 19, 20 and the sample flash tank 3. Several conduits may be provided which can be used separately or simultaneously.

In a preferred embodiment, the conduits 2 are provided with at least two sampling valves 4, 5. The valves are preferably placed as close to the reactor as is possible due to the limitations of valve size fittings, etc. Preferably, between the valves 4 and the reactor 19, 20, flushing means are provided in order to avoid plugging and blocking of the conduit part between the valves 4 and the reactor 19, 20.

The conduits 2 are provided with means for periodically sequentially opening and closing said valves 4, 5. The mechanism of closing and opening the valves 4, 5 is as follows: first the first valve 4 is opened while maintaining said second valve 5 closed, then said first valve 4 is closed while maintaining said second valve 5 closed, subsequently, the second valve 5 is opened while maintaining said first valve 4 closed and finally, said second valve 5 is closed while maintaining said first valve 4 closed. According to this mechanism, the valve closest to the reactor 4 is open while the second valve 5 is closed. The volume between the two valves is filled with slurry coming from the reactor. The valve near the reactor 4 is closed and the second valve 5 is opened. As the pressure is lowered, the slurry flashes and pushes the product to a sample flash tank 3. Valve 4 is open only long enough to take a sufficient sized sample such that analytical error is minimised. Preferably the sequence of opening and closing the valves 4, 5 follows fixed time limits. By way of illustration, a suitable sequence of opening and closing the valves may comprise opening of the valve 4 between two and ten seconds, and preferably for four seconds, while keeping valve 5 closed; followed by closing the first valve 4 between one and five seconds, and preferably for two seconds while keeping the second valve 5 closed: opening the valve 5 between two and twenty seconds, and preferably for six seconds, while valve 4 remains closed and closing the valve 5 between one and sixty seconds, and preferably for five seconds while keeping the valve 4 closed. After this sequence, the sequential mechanism can be repeated.

The size of the sample is determined by the volume of pipe, which extends between valve 4 and valve 5, which is closed during the sampling of the reactor. Typically, an effective analysing amount will be a minor volume proportion of the amount produced by the polymerisation reactor. In a preferred embodiment the size of the sample volume is adapted by providing different conduits lengths and thus different volumes of pipe extending between valve 4 and valve 5. According to the present invention, taking a relative small amount of sample from said reactor provides reliable data on the polymerisation reaction in the reactor.

A small amount of sample in this invention means the smallest possible amount of material that it is technically feasible to withdraw. Accordingly, the size of the sample flash tank is less than 10%, preferably less than 1%, more preferably less than 0.1% of that of a single flash tank of a size adapted to that of the reactor.

In addition, the device provides additional flushing valves 38, provided on the conduit downstream the first valve 4 and upstream the second valve 5. These valves 38 play a role in an automatic flushing mechanism, which is activated after taking a sample from the reactor. Automatic flushing enables cleaning and rinsing of the sample volume in the conduit with diluent, in particular isobutane, and keeps the conduit free.

When taking a sample from the reactor, the sequential opening/closing mechanism of the valves 4, 5 is activated. Interruption of said sequential mechanism stops sample out take and activates the automatic flushing mechanism. During automatic flushing the first valve 4 remains open together with the flushing valve 38, in order to provide continue flushing to the reactor such that plugging is avoided. The flushing valve 38 is always closed prior to opening valve 5. By way of illustration, a suitable sequential mechanism for activating the automatic flushing mechanism is as follows: the first valve 4 is closed, the flushing valve 38 is closed and the second valve 5 is opened, preferably for ten seconds, and subsequently closed again. The flushing valve 38 is then opened, between five and thirty seconds, and preferably for fifteen seconds and closed again. The second valve 5 is subsequently re-opened preferably for ten seconds and then closed. The flushing valve 38 is opened and remains open, while also the first valve 4 is opened and remains open.

When a novel sample needs to be taken out of a reactor, the automatic flushing mechanism needs to be interrupted, which preferably takes place as follows: the flushing valve 38 is closed and remains closed, the first valve 4 is closed. The second valve 5 is opened during preferably ten seconds and closed again, while the flushing valve 38 is closed. After preferably twenty to thirty seconds, the sequential mechanisms of opening and closing the valves 4, 5 as described above, can be re-activated in order to obtain a sample in the conduit volume provided between said valves 4, 5.

When the valves 4 near the reactor 19 are opened, the sample is introduced in the conduit 2 and a sample volume is further transported to the sample flash tank 3, by means of sample flash lines 22. In a preferred embodiment, the slurry is provided at the entrance of the sample flash tank at a suitable temperature and pressure such that the slurry is entered into the sample flash tank in gas form.

Preferably the pressure in reactor 19 is around 43 bars. In the sample flash lines, the pressure is reduced in order to reach a pressure preferably comprised between 1.1 bar and 3 bar in the sample flash tank 3. The major drop in pressure preferably takes place at the second valve 5, and is further linearly reduced between the second valve 5 and the sample flash tank 3 in the flash lines 22.

In a preferred embodiment, said sample flash lines 22 are constructed as jacketed pipes, i.e. double envelope tube exchangers. The sample flash lines 22 consist of an inner tube for transporting the sample, and an outer tube, provided as a coat on said inner tube, which can be heated, e.g. by means of a steam stream flowing through said outer tube. Heating of the sample improves and facilitates further purification of the sample and increases the degassing efficiency in the sample flash tank, which guarantees a reliable and accurate gas analysis. Preferably the size of the sample flash lines 22 is chosen in order to have the slurry at a correct temperature entering the sample flash tank 3. The size of the sample flash lines 22 is also chosen in order to obtain a suitable velocity of the slurry. The temperature in the coating tube is preferably regulated by adapting steam pressure by means of steam pressure controlling means 23. It is preferred that the temperature in the sample flash tank is at least higher than 35° C. and preferably higher than 50° C.

The slurry transferred through conduit 2 and 22 is provided to a sample flash tank 3 wherein a more complete separation between the polyethylene and the unreacted reactants including ethylene, hexene, hydrogen and isobutane occurs. Preferably, said sample flash tank 3 consists of a tubular body 9 and a conical bottom 10.

Providing a suitable temperature and pressure in the sample flash tank 3 enables to increase the degassing efficiency in the sample flash tank and to obtain a substantially degassed polyethylene powder remaining in the tank. Increased degassing efficiency also permits to increase the accuracy of the gas analysis performed on a portion of the gas removed from the sample flash tank. The sample flash tank 3 is heatable. The tubular body 9 is provided with a heatable coat 39 and the conical bottom 10 is preferably provided on its surface with conduits 11 wherein steam or hot water can be provided. Preferably, the temperature in the sample flash tank is higher than 35° C., and even more preferred, higher than 50° C. The pressure in the sample flash tank 3 will vary depending on the nature of the diluent and monomer and the temperature selected. Preferably, according to the present invention, the pressure value in the sample flash tank 3 comprises between 1.1 and 3 bar and more preferred between 1.5 and 1.6 bar. In the sample flash tank 3 free unreacted ethylene, isobutane, hexene co-monomer and hydrogen are released as vapor; any hydrocarbons trapped in the pores of the polymer powder are carried away.

Flash gas, comprising essentially unreacted ethylene, isobutane, hexene co-monomer and hydrogen, is removed from the sample flash tank 3 through a conduit 24, preferably provided at the top of the sample flash tank 3. Means 26 are preferably provided on conduit 24 which regulate the pressure in said conduit such that the pressure is higher upstream the means 26 than downstream the means, in order to avoid reflux of the gases from the reactor, which could induce a deficient off gas analysis. Preferably, the pressure from the sample flash tank is used as control, and the means 26 installs a pressure, which preferably exceeds the flash tank pressure with 100 mbar.

The flash gas, which is a mixture of unreacted reactants, is preferably transferred to a recycle section 31, wherein the gas is compressed, the reactants are separated from the mixture, and fed to the polymerisation reactor if desired at a suitable flow rate.

A sample of the fluid (gas) flowing through the conduit 24 is provided to a gas analyser 7 through conduit means 25. Samples taken from the vapor phase are indicative of the compositions in the vapor phase existing in the reactor. The analyser 7 is preferably a chromatographic analyser. The analyser 7 provides an output signal, which is representative of the concentration of one or several reactants in the fluid flowing through conduit 24. Essentially, this signal is representative of the concentration of unreacted ethylene, hexene, and hydrogen removed from reactor 19. The signal can be provided from the analyser 7 as an input to a computer. In response to this signal, the computer may determine the concentration of unreacted ethylene, hexene, and hydrogen in the reactor 19 and determines whether adjustment of ethylene, hexene, and hydrogen flow to the reactor 19 is needed. Additionally, instead of adjusting these feeds, the system also could be set up so that other or additional reactants such as diluent (isobutane) feed or catalyst feed are adjusted in response to a signal from the computer.

A solid fraction or powder essentially consisting of PE and dissolved isobutane and co-monomer is collected at the bottom of the sample flash tank 3 from which it is transferred to sample receivers 6 for further purification. Transfer of the powder is done by means of a conduit 12, provided with at least two valves 13, 14. Said conduit 12 is preferably provided with means for periodically sequentially opening said first valve 13 while maintaining said second valve 14 closed, closing said first valve 13 while maintaining said second valve 14 closed, opening said second valve 14 while maintaining said first valve 13 closed and closing said second valve 14 while maintaining said first valve 13 closed. This mechanism allows a well-defined amount of powder to be transferred to the sample receiving means 6. The valves also avoid the entrance of nitrogen, provided downstream in the system, into the sample flash tank 3. Preferably, the sampling device is further provided with means 27 for purging with wet nitrogen, preferably downstream the second valve 14 on conduit 12. Providing wet nitrogen enables to kill residual alkyl and catalyst in the powder.

Powder removed from the sample flash tank 3 through conduit means 12 will be treated to remove any remaining co-monomer and diluent. Such treatments preferably include degassing and drying in a sample receiver 6. Preferably, said sample receiver 6 consists of a tubular body 15 and a conical bottom 16. The sample receiver 6 is heatable. The conical bottom 16 is preferably provided on the surface with conduits 11 wherein steam or hot water is provided. It is preferred to heat up the receivers in order to increase the degassing efficiency and purification in the sample receiver. Preferably, one sample flash tank 3 may be connected to several sample receivers 6 by means of the conduit 12. In order to alternately send powder to the one or the other receiver 6, a diverter 18 is provided, downstream the second valve 14 and upstream of the sample receivers 6 on said conduit 12.

Generally, PE powder is collected in one sample receiver 6, which is in connection with means 8 for analysing said polymer powder. If it is necessary to take a sample for analysis, or to switch to another receiver 6. e.g. when one of the receivers is full and needs to be emptied, the PE powder can be directed, by regulation of the diverter 18, to a second sample receiver, while the first receiver can at the meantime be drained. Subsequently, the flash tank is again connected to the first receiver, and from the second receiver a sample can be taken for analysis.

In particular, the purpose of the sample receivers 6 is to strip hydrocarbons trapped in the pores of the polymer. This is preferably done with a long residence time in the receiver and a nitrogen sweep. The sample receivers 6 comprise means 28 for providing nitrogen, preferably at the bottom of said receiver 6. Providing nitrogen to the receiver enables to further purge and purify the PE powder in the receiver 6. Nitrogen flushed in the receivers can be removed by means of a conduit 29 to a collecting vessel 30, e.g. seal oil pot, which may be common for two or several sample receivers 6. From this collecting vessel, nitrogen is released to the atmosphere. In addition, the sample receivers 6 can be further provided with means for measuring explosiveness.

In another preferred embodiment, the sample receivers 6 are provided with a filter 17, preferably at the top of the tubular body 15 of the receivers 6, for avoiding powder fines to be swept away with the conduit 29 releasing nitrogen. These filters preferably are bag filters having a nitrogen pulse-jet for cleaning.

The sampling device according to the present invention comprises several protection mechanisms in order to correctly and efficiently control operations of the sampling device. For instance, when the pressure becomes too high in the sample flash tank or when a high level is reached in the sample flash tank, the sampling sequential mechanism is stopped and automatic flushing is activated. When a very high pressure is obtained in the sample flash tank, the valves 4, 5 and the flushing valves 38 are closed. In another example, one sample receiver can be drained and emptied, when the diverter 18 is oriented towards another sample receiver, provided explosiveness is sufficiently low. Another control system consists of diverting the transfer of PE powder from the sample flash tank 3 to another sample receivers 6 when a high level is obtained in a first sample receiver. The transfer of PE powder from the sample flash tank 3 to the sample receivers 6 via conduit 12 can be interrupted in case of a high pressure in the sample flash tank 3 or a high level in the sample receivers 6. Another control system consists of closing the conduit to the gas analyser 7 in case a high pressure is obtained in the sample flash tank 3. Furthermore, when a low pressure is registered in the polymerisation reactor 19, the sampling sequence mechanism is stopped and automatic flushing is activated.

Figure 2:
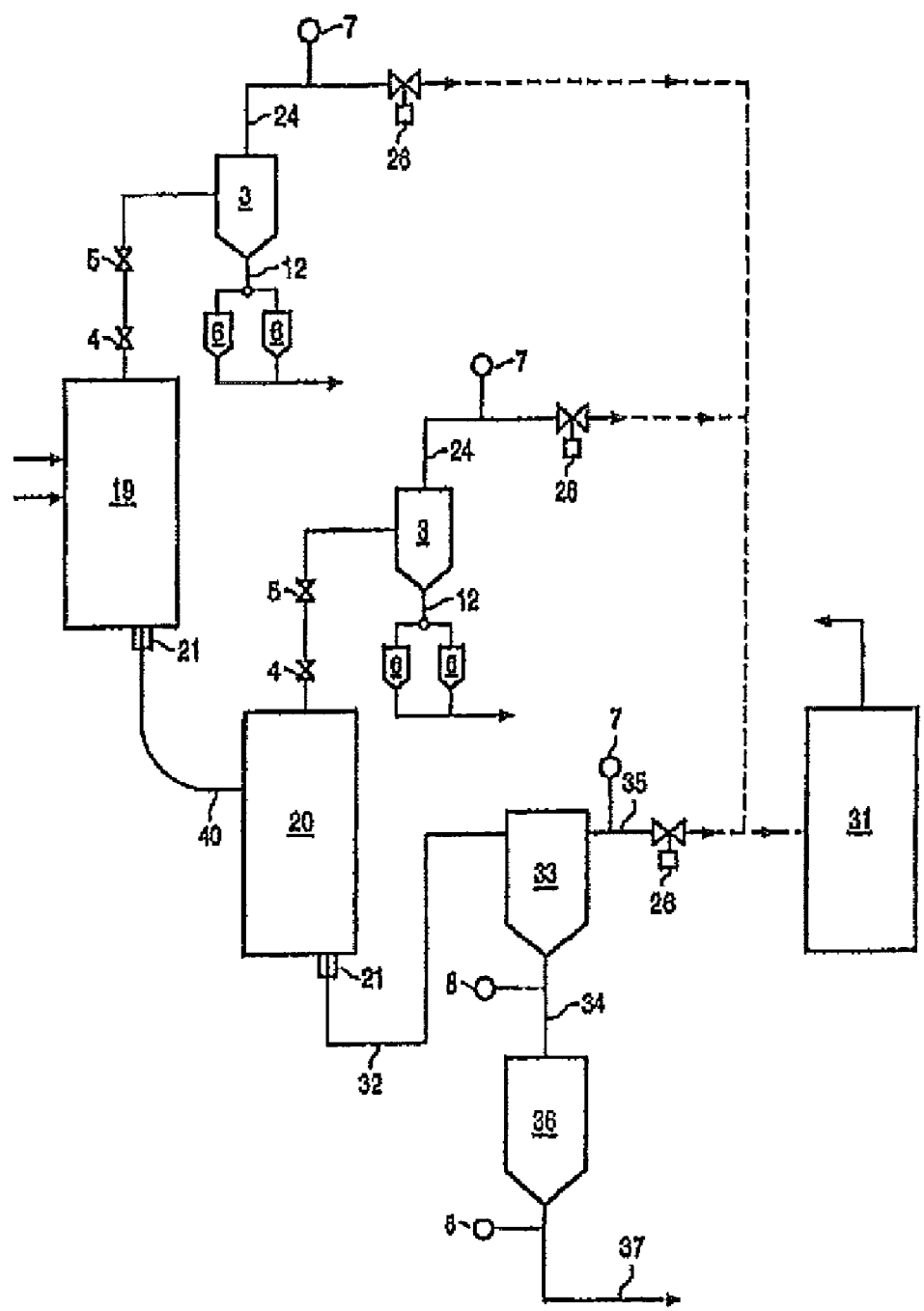
FIG. 2 is a schematic representation of a polymerisation reaction and recovery system, which utilises a sampling device according to the present invention.

Referring now to FIG. 2, a schematic representation of a polymerisation reaction and recovery system, which utilises sampling devices according to the present invention, is illustrated. The figure shows two liquid full loop reactors, comprising a first 19 and a second reactor 20 connected in series by one or more settling legs 21 of the first reactor connected for discharge of slurry from the first reactor 19 to said second reactor 20. Such configuration can be applied for manufacturing bimodal PE. Each reactor 19, 20 is provided with a sampling device 1 according to the invention. Preferably, in case two reactors are used, the pressures in the first reactor 19, is preferably comprised between 43 and 44 bar, while the pressure in the second reactor comprises between 41 and 42 bar. The pressure is generally lower in the second reactor compared to the first reactor to ensure a sufficient flow rate.

The process for manufacturing bimodal PE is known in the art and for instance disclosed in U.S. Pat. No. 5,639,834, which describes a process for the co-polymerisation of ethylene in two liquid full loop reactors in series wherein high and low average molecular weight polymers are produced respectively in a first and a second reactor. The reaction conditions in the first and the second reactors are different in order to obtain high and low average molecular weight polymers respectively in the first and second reactor. The ethylene polymer stream obtained in the first reactor is transferred to the second loop reactor through one or more settling legs of the first reactor, e.g. using six settling legs each one being independently filled with reactor slurry, solids being concentrated by gravity settling, and discharged.

For taking a sample of slurry that is produced in the reactors 19, 20 in such configuration, for off gas analysis and determination of the characteristics of the produced gas composition and PE powder, a specific sampling device according to the present invention is provided on the first reactor 19 or on both the first 19 and the second reactor 20, as illustrated on FIG. 2. However, it should be clear that the sampling device according to the present invention is also very suitable for use on individual reactors for manufacturing polyethylene, or on reactors for manufacturing of monomodal PE. "Monomodal PE" is produced using two reactors, which are operating in parallel. In accordance with such reactors, the sampling device according to the present invention can be provided on both reactors.

As illustrated on FIG. 2, the following reactants are provided to polymerisation reactor 19: ethylene, hexene-1 co-monomer, isobutane diluent, a catalyst and hydrogen. The several reactants can be introduced to the reactor by means of one or several conduits. The majority of the reaction effluent, i.e. polymerisation slurry, is removed from the reactor 19 by one or more settling legs 21 of the first reactor and discharged from the first reactor 19 to said second reactor 20. A sampling device 1 according to the invention is connected to said first reactor 19. Slurry removed through conduit means 2 and 22 is provided to a sample flash tank 3. In the sample flash tank 3 vaporisation of the monomer, co-monomer, hydrogen and diluent occurs: however, vaporisation can also occur at least partially within conduit 22. Unreacted reactants are removed from sample flash tank 3 through conduit means 24. A sample of the gas flowing through conduit means 24 is provided to an analyser 7, preferably a chromatographic analyser. The remaining gas flowing through conduit 24 can be recycled by means of a recycle section 31, and the separated reactants can be fed to the polymerisation reactor 19 if desired. Solid polyethylene is provided from the sample flash tank 3 through conduit means 12 to a sample receiver 6. The reaction conditions in the first reactor are monitored by means of a sampling device according to the present invention. Based on the results obtained from this analysis, the reaction conditions in the first reactor are adapted in order to obtain an optimal reaction product leaving the first reactor 19.

Slurry is transferred from the first 19 to the second reactor 20 by means of lines 40. Transfer of slurry from one to another reactor is preferably continuously performed by using the settling legs 21.

The second reactor 20 is further connected by means of flash lines 32 to a flash tank 33, unreacted reactants are separated from the incoming slurry in said flash tank 33. Polyethylene powder is removed from the tank 33 through conduit means 34 which conduct the polyethylene powder to a purge column 36. Within the flash tank 33 unreacted reactants are removed as vapor from flash tank 33 via conduit 35. The gas flowing through conduit 35 can be transferred to a recycle section 31, where the reactants in the gas are separated and if desired again fed to the polymerisation reactor 19. The conduit 35 can be further provided with a gas analyser 7 for analysing a portion of the gas flowing through said conduit 35. PE powder removed from the flash tank 33 will be further treated to remove any remaining co-monomer and diluent by providing it to a purge column 36, where after PE is further removed through conduit means 37. Analysis of the PE powder can be done by means of analysing means 8 which are provided in connection to conduit 34 or to conduit 37. Preferably, means 8 provided in connection to conduit 34 are utilised when the residence time in the purge column 36 is long, while means 8 provided in connection to conduit 37 can be utilised when the residence time in the purge column 36 is short.

Again, a sampling device according to the invention can be connected to said second reactor 20, in order to take a sample and analyse a sample from the second reactor 20. Slurry removed through conduit means 2 and 22 is provided to a sample flash tank 3. Unreacted reactants are vaporised and removed from sample flash tank 3 through conduit means 24. A sample of the gas flowing through conduit means 24 can be provided to a gas analyser 7, preferably a chromatographic analyser. The remaining fluid flowing through conduit 24 can be compressed and recycled back to the polymerisation reactor 19 or 20 after passage through a recycle section 31 if desired. PE powder is provided from the sample flash tank 3 through conduit means 12 to a sample receiver 6 for further purification.

In another preferred embodiment, it is to be understood that where necessary flushing and purging means and lines are available on the sampling device according to the invention in order to avoid plugging, blocking or explosiveness risk.

With reference to FIG. 2, it should be noted that the sample flash tank 3 and the sample receivers 6, preferably have a similar configuration as the flash tank 33 and the purge column 36, respectively, but are relatively much smaller than the flash tank 33 and the purge column 36. In a preferred embodiment, the sample flash tank 3 and the sample receivers 6 are at least 10 times, and preferably 100 times and even more preferred 1000 times smaller than the flash tank 33 and the purge column 36. This indicates that according to the invention small volumes of samples, preferably around 40 cm$^3$, are sufficient to provide accurate and reliable data on the reaction in a reactor.

In another aspect the present invention relates to a method for improving a polymerisation reaction in a polymerisation reactor. In one aspect the method comprises the improvement and optimisation of a polymerisation reaction in an individual polymerisation reactor. In an embodiment said method comprises the steps of
  a) taking a sample out of said reactor, preferably by means of a sampling device according to the present invention.
  b) analysing said sample to determine said reaction conditions in said reactor, and
  c) based on results obtained in step b), adapt reaction conditions in order to improve the polymerisation reaction in said reactor.

In another aspect, the method comprises the improvement and optimisation of a polymerisation reaction in a polymerisation reactor, which consists of several parts or several reactors, which are connected to each other in series. Preferably said polymerisation reaction comprises the polymerisation of ethylene to prepare bimodal polyethylene in a first and a second reactor which are connected to each other. Said method comprises the steps of:
  a) taking a sample out of said first (part of said) reactor 19
  b) analysing said sample to determine said reaction conditions in said first (part of said) reactor 19.
  c) based on results obtained in step b), adapt reaction conditions in said first and second (parts of the said) reactor in order to improve the polymerisation reaction in said first and second (parts of said) reactor.

In a preferred embodiment, said method comprises the steps of
  a) taking a sample out of said first (part of said) reactor 19,
  b) analysing said sample to determine said reaction conditions in said first (part of said) reactor 19,
  c) based on results obtained in step b), adapt reaction conditions in said first (part of said) reactor 19 in order to provide an optimised reaction product in said first (part of said) reactor, and
  d) transferring said reaction product from said first (part of said) reactor 19 to said second (part of said) reactor 20,
  e) optionally, based on results obtained in step b), adapt reaction conditions in said second (part of said) reactor in order to provide an optimised reaction product in said second (part if said) reactor, and
  f) transferring at a suitable time said optimised reaction product from said second (part of said) reactor 20 to further processing means.

In a particularly preferred embodiment, the method comprises providing a reactor wherein said first part and said second part of said polymerisation reactor consists of a first 19 and a second 20 liquid loop reactor, connected to each other in series, wherein the first reactor 19 has one or more settling legs 21 for discharge of slurry from the first reactor 19 to said second reactor 20. The method is particularly suitable for being applied for improving a polymerisation reaction in a polymerisation reactor during a process for preparing bimodal polyethylene. For preparing bimodal polyethylene, two polymerisation reactors are used that are connected to each other in series, as e.g. illustrated on FIG. 2.

The present invention provides a method for monitoring and optimising the operational conditions in a first reactor in the polymerisation process for obtaining polyethylene. The method consists of taking a sample taken out of reactor, analysing said sample to determine the operation reaction conditions in the first reactor. A sampling device according to the invention is preferably provided on said first reactor and enables to analyse a sample from said reactor and to determine the reaction conditions in the first reactor. Based on the analyses results obtained, one can adapt or fine-tune the operational reaction parameters in the first reactor if required, in order to improve the polymerisation reaction in said reactor and to obtain polyethylene having the desired properties.

Preferably, sampling is performed continuously and the samples are analysed frequently, in order to accurately follow up the polymerisation reaction in the first reactor. Analysis of these samples is preferably done at defined time points. Preferably, a PE powder sample obtained from the sample receivers 6 is analysed every one or two hours, and a gas sample, obtained from the sample flash tank 3 is analysed automatically every five to fifteen minutes.

In another embodiment, the sampling device according to the invention can be provided on both a first and a second reactor. By additionally providing a sampling device according to the invention on the second reactor, samples from said second reactor can be continuously taken and frequently analysed and one is capable of following up the reaction conditions and the polymerisation reaction in the second reactor, and adapt operational reaction parameters if required, to improve the polymerisation reaction and to obtain an end product having the desired properties. Once the reaction product of the first reactor has been transferred to the second reaction the method may further comprise taking a sample out of the second reactor; analysing said sample to determine said reaction conditions in said second reactor and based on results obtained on the reaction conditions, fine-tune and adapt the reaction conditions in the second part of said reactor in order to provide a optimised reaction product as a result of the reaction in said second part of in said reactor.

The method further allows determining the suitable moment for transferring the reaction product having optimal desired properties to further processing means. Transfer of a reaction product having optimal properties at an optimal moment for further processing, considerably improves the quality of the obtained reaction product.

The different properties of the polyethylene (molecular weight, density, . . . ) can be adjusted by controlling operating parameters of the reactors such as temperature, ethylene concentration, hexene concentration, hydrogen concentration, residence time. Other reactor parameters could be controlled as well, such as reactor pressure, solid concentration inside the reactor and catalyst productivity, powder properties, etc. . . . .

In another preferred embodiment, the method comprises taking a specific volume of a sample from said first part 19 of said reactor. This can be obtained by using a specific sampling mechanism. The method consists of providing valves 4, 5 on conduits 2 connecting the reactor 19 with a sample flush tanks 3, having means for periodically sequentially opening and closing said valves 4, 5. The mechanism of closing and opening the valves 4, 5 is described in more detailed above. The size of the sample is determined by the volume of pipe, which extends between valve 4 and valve 5.

In a further embodiment, the present invention relates to a method, wherein step a) wherein a sample is taken comprises
providing a sample from said first part 19 of said reactor to a sample flash tanks 3, by transferring said sample though a conduit 2 connecting said first part 19 of said reactor to said sample flash tank 3,
separating in said sample flash tank 3 solid particles from evaporated gas in said sample by controlling the pressure in said flash tank 3,
supplying said solid particles from said sample flash tank 3 to one or more sample receivers 6, by transferring said solid particles though a conduit 12 connecting said sample flash tank 3 and said sample receivers 6, and
purifying said solid particles in said sample receivers 6, by degassing and drying.

In addition, in another further embodiment, the step b) in the present method comprises analysing evaporated gas obtained from said sample flash tanks 3 with analysing means 7, and analysing solid particles obtained from said sample receivers 6 with analysing means 8.

While the invention has been described in terms of the presently preferred embodiment, reasonable variations and modifications are possible by those skilled in the art and such variations are within the scope of the described invention and the appended claims.

EXAMPLE

The following example illustrates the effectiveness of the present invention in better controlling polymerisation conditions and subsequently polymer properties.

The reactor used herein is a commercial double loop reactor with the two loops in sequential configuration equipped with a sampling system as described in the present document.

The reactor is used to produce a bimodal polyethylene resin. Polymerisation conditions are controlled on both reactors to ensure suitable product properties.

Figure 3:
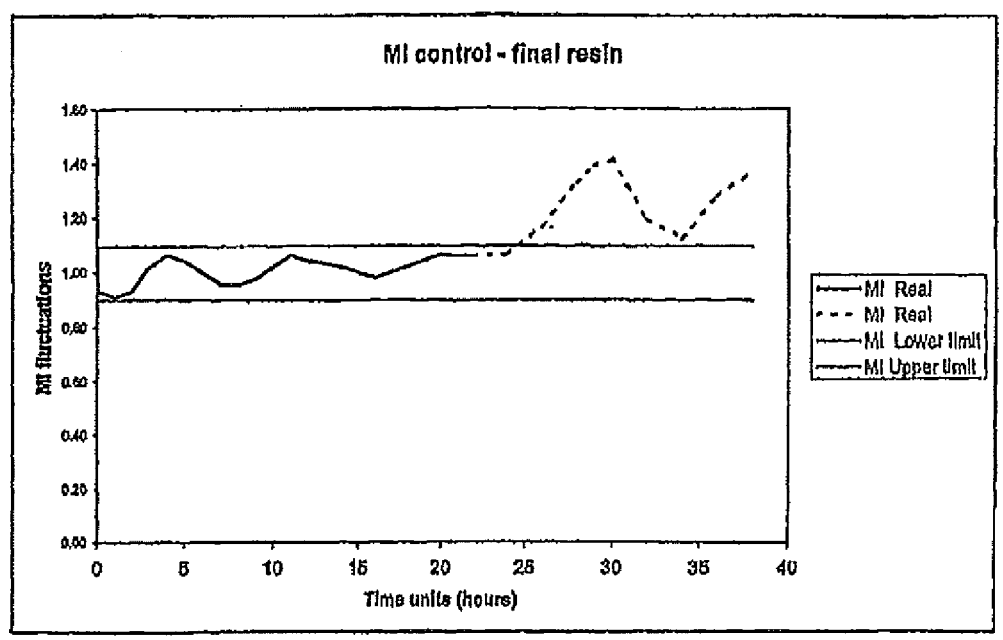
FIG. 3 shows the effect of using the present invention for controlling polymerisation conditions for a bimodal polyethylene.

FIG. 3 shows the effects of using the sampling system of the present invention for controlling polymerisation conditions on the melt flow index of a bimodal polyethylene. FIG. 3 displays the evolution of the scaled melt index over time. The scaled melt index is calculated after completion of the production run in the following way: From the melt flow indices measured during the first 21 hours an average melt flow is calculated. The scaled melt flow index ("MI fluctuations") is the quotient of the actual real melt flow and the averaged melt flow index of the first 21 hours. For a perfectly controlled system the quotient assumes a value of 1.

In FIG. 3 the first 21 hours show the evolution of the scaled melt flow index when the sampling system of the present invention was in use. The use of the sampling system permits to control the melt flow index of the bimodal polyethylene within very narrow specifications.

After 21 hours the sampling system of the present invention was turned off. This immediately led to a significant increase in the fluctuation of the melt flow index in the bimodal polyethylene.

The data clearly shows that the sampling system of the present invention allows for better control of polymerisation conditions and consequently of final product properties.

The invention claimed is:

1. A system for the recovery of a polymer sample from a polymerization reactor comprising:
    a polymerization reactor for the polymerization of an olefin monomer in a liquid diluent to form an olefin polymer;
    a sample conduit connected to said polymerization reactor for receiving a sample of polymer particles in said liquid diluent from said polymerization reactor;
    a sample release valve disposed in said conduit;
    an automatic flushing mechanism in fluid connection with the sample conduit;
    a flash tank operably connected to said conduit effective for the separation of said diluent from polymer particles and comprising an inlet connected through a flash line to the outlet of said sample release valve, a first outlet for the removal of polymer particles from said flash tank and a second outlet for the release of gas from said flash tank;
    a sample receiving chamber having an inlet for receiving the polymer sample and an analyzer; and
    a sample transfer line extending from said flash vessel to said sample receiving chamber and provided with at least one valve with the outlet of said valve connected to said sample receiving chamber.

2. The system of claim 1, wherein said sample conduit comprises a sample input valve spaced from said sample release valve in the direction of said reactor.

3. The system of claim 2, wherein second outlet of said flash tank is provided with a gas release line for the removal of gas from said flash tank.

4. The system of claim 3, wherein the gas release line from said second outlet is provided with a gas analyzer evaporated from said flash vessel.

5. The system of claim 2 further comprising a controller for sequentially operating said sample input valve and said sample release valve in said sample conduit in a sequence in which said sample input valve is open while sample release valve is closed followed by a sequence in which said sample release valve is open while said sample input valve is closed.

6. The system of claim 1 wherein said sample receiving chamber has a purge gas inlet line for the introduction of a purge gas into said sample receiving chamber and a purge gas outlet line for the recovery of purge gas.

7. The system of claim 6 wherein said sample receiving chamber is provided with a filter interposed between the interior of said sample release chamber and the purge gas outlet line from said sample release chamber.

8. The system of claim 7 further comprising a collection vessel connected to said purge gas outlet line.

9. The system of claim 1, wherein the sample transfer line extending from said flash tank to said sample receiver is provided with a first outlet valve in proximity to said flash tank and a second outlet valve spaced from and connected in series with said first outlet valve.

10. The system of claim 9, wherein the sample transfer line from said flash tank is provided with a flow controller for sequentially operating said first and second outlet valves in which said first valve is opened while maintaining said second valve closed and thereafter closing said first valve while opening said second valve for the transfer of polymer sample from said flash tank to said sample receiving vessel.

11. The system of claim 9, wherein said flash tank is provided with a heater for heating the contents of said flash tank.

12. The system of claim 9 further comprising a second sample receiving chamber in parallel with said first recited sample receiving chamber and further comprising a diverter valve in said sample transfer line connected downstream of said second outlet valve for alternatively connecting the outlet of said flash chamber to one of said sample receiving chambers while retaining the other said sample receiving chamber offstream.

13. The system of claim 12 further comprising a purge line interconnected to said sample transfer line between said outlet valves and the said diverter valve.

14. The system of claim 1 further comprising a second polymerization reactor and a polymer transfer line for the transfer of polymer slurry from said first reactor to said second reactor, said second reactor further comprising a sampling system.

15. The system of claim 14 further comprising a settling leg connected to said second reactor for recovery of polymer slurry from said second reactor, a polymer outlet line extending from said settling leg to a flash recovery vessel having a first outlet for removal of gas therefrom and a second outlet for the transfer of polymer particles and a purge vessel connected to said second outlet for the recovery of polymer particles from said flash recovery vessel.

* * * * *